United States Patent [19]

Watanabe et al.

[11] 4,165,369
[45] Aug. 21, 1979

[54] LIQUID HAIR RINSE CONTAINING QUATERNARY AMMONIUM SALTS AND A SYNTHETIC SECONDARY ALCOHOL

[75] Inventors: Hiroshi Watanabe; Toshihiro Shirose; Eiji Iijima, all of Chiba, Japan

[73] Assignee: Kao Soap Co., Ltd., Tokyo, Japan

[21] Appl. No.: 891,755

[22] Filed: Mar. 30, 1978

Related U.S. Application Data

[63] Continuation of Ser. No. 713,650, Aug. 12, 1976, abandoned.

[30] Foreign Application Priority Data

Sep. 11, 1975 [JP] Japan .................... 50-110301

[51] Int. Cl.² ............................................. A61K 7/08
[52] U.S. Cl. ............................................. 424/70; 252/106; 252/544; 252/547; 424/365
[58] Field of Search ............... 424/70, 365; 252/544, 252/547, 106

[56] References Cited

U.S. PATENT DOCUMENTS

| | | | |
|---|---|---|---|
| 3,101,300 | 8/1963 | Siegel et al. | 424/70 |
| 3,155,591 | 11/1964 | Hilfer | 424/70 |
| 3,228,842 | 1/1966 | Markland et al. | 424/70 |
| 3,272,712 | 9/1966 | Kalopissis et al. | 424/70 |
| 3,322,676 | 5/1967 | Hiestand | 424/70 |
| 3,341,465 | 9/1967 | Kaufman et al. | 424/70 |
| 3,423,504 | 1/1969 | Birkelo et al. | 424/70 |
| 3,577,528 | 5/1971 | McDonough et al. | 424/70 |
| 3,578,719 | 5/1971 | Kalopissis et al. | 424/70 X |
| 3,812,046 | 5/1974 | Lancz | 252/547 X |
| 3,822,312 | 7/1974 | Sato et al. | 424/70 X |
| 3,892,669 | 7/1975 | Rapisarda et al. | 252/547 X |
| 3,896,034 | 7/1975 | Eckert et al. | 252/547 X |

Primary Examiner—James O. Thomas, Jr.
Assistant Examiner—Vera C. Clarke
Attorney, Agent, or Firm—Blanchard, Flynn, Thiel, Boutell & Tanis

[57] ABSTRACT

A hair rinse composition comprising as indispensable components (A) 0.1 to 10% by weight of at least one quaternary ammonium salt having the formula (I):

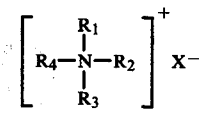

wherein $R_1$, $R_2$, $R_3$ and $R_4$ each is alkyl, hydroxyalkyl or benzyl, with the proviso that one or two of $R_1$, $R_2$, $R_3$ and $R_4$ is alkyl or hydroxyalkyl having 8 to 20 carbon atoms and the remainder of $R_1$, $R_2$, $R_3$ and $R_4$ are alkyl or hydroxyalkyl having 1 to 3 carbon atoms, or benzyl, and X is an anion, and (B) 0.1 to 10% by weight of a secondary alcohol or ethoxylate thereof in which the average mole number of added ethylene oxide units is zero to 7 and the alkyl group has 8 to 20 carbon atoms.

10 Claims, No Drawings

LIQUID HAIR RINSE CONTAINING QUATERNARY AMMONIUM SALTS AND A SYNTHETIC SECONDARY ALCOHOL

This is a continuation of application Ser. No. 713,650 filed Aug. 12, 1976, now abandoned.

BACKGROUND OF THE INVENTION

1. Field of the Invention

The present invention relates to a hair rinse composition which possesses an excellent rinsing effect and which imparts smoothness and suppleness to human hair. More particularly, the present invention relates to a hair rinse composition comprising, as indispensable components, a quaternary ammonium salt and a secondary alcohol or ethoxylate thereof in which the average mole number of added ethylene oxide units is zero to 7 and the alkyl group has 8 to 20 carbon atoms.

2. Description of the Prior Art

Hair rinse compositions comprising as an effective component a quaternary ammonium salt have heretofore been used for alleviating troublesome characteristics of freshly-washed hair such as rough feel, entanglement, generation of static charges and difficulty in combing. The hair rinse compositions impart softness, smoothness and an antistatic property to hair. However, when a quaternary ammonium salt alone is used, fully satisfactory effects of smoothness and softness cannot be obtained. In order to overcome this disadvantage of the use of the quaternary ammonium salt alone, oils and fats such as higher alcohols, glycerides and liquid paraffins have heretofore been incorporated in hair rinse compositions.

The oils and fats that have heretofore been used are not fully satisfactory as regards the rinsing effect and they are not effective for use on damaged hair, for example, hair which has been subjected to dyeing and cold wave treatments. Further, even if temporarily satisfactory effects are attained, they do not last and, as is well known, the effects attained by rinsing are lost immediately after hair is dried.

SUMMARY OF THE INVENTION

We have discovered that when a long-chain alkyl secondary alcohol or ethoxylate thereof in which the alkyl group has 8 to 20 carbon atoms and the average mole number of added ethylene oxide units is zero to 7 is used in combination with quaternary ammonium salts in hair rinse compositions, an unexpectedly superior rinsing effect is obtained.

More specifically, in accordance with the present invention, there is provided a hair rinse composition comprising as critical components (A) from 0.1 to 10, preferably 0.5 to 7, more preferably 1 to 4, % by weight of a quaternary ammonium salt, or a mixture of quaternary ammonium salts, having the following formula (I):

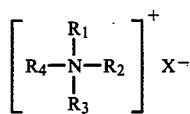

wherein $R_1$, $R_2$, $R_3$ and $R_4$ each is alkyl, hydroxyalkyl or benzyl, with the proviso that one or two of $R_1$, $R_2$, $R_3$ and $R_4$ is alkyl or hydroxyalkyl having 8 to 20 carbon atoms, and the remainder of $R_1$, $R_2$, $R_3$ and $R_4$ are alkyl or hydroxyalkyl having 1 to 3 carbon atoms, or benzyl, and X is an anionic group selected from the group consisting of halide, methylsulfate ($-CH_2SO_4$) or ethyl sulfate ($-C_2H_5SO_4$). As the halide, it is preferred to employ the chloride, bromide or iodide, more preferably the chloride and bromide, and (B) 0.1 to 10% by weight of a secondary alcohol or ethoxylate thereof in which the average mole number of added ethylene oxide units is zero to 7, preferably zero to 3, and the alkyl has 8 to 20, preferably 12 to 18, carbon atoms.

The secondary alcohol or its ethoxylate that is used in the present invention is a synthetic alcohol prepared by oxidizing normal paraffin or an ethylene oxide adduct of this synthetic alcohol. It has the formula

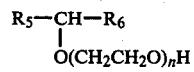

wherein

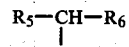

is alkyl having 8 to 20 carbon atoms and n is an integer from zero to 7. When the mole number of added ethylene oxide units is larger than 7, the ethoxylate has an increased water solubility and is ineffective as an oil for improving the rinsing effect.

The secondary alcohol or its ethoxylate is incorporated in the hair rinse composition of the present invention in an amount of 0.1 to 10% by weight, preferably 0.5 to 5% by weight, more preferably 1 to 4% by weight.

The hair rinse composition of the present invention is prepared by mixing a quaternary ammonium salt or a mixture of salts having the above formula, with the secondary alcohol or its ethoxylate, and dissolving the mixture in water and a suitable solvent, for example, ethylene glycol, ethyl alcohol, glycerin or propylene glycol. If needed, additives heretofore conventionally used in hair rinse compositions, such as oils and fats, for example, higher alcohols, glycerides, hydrocarbons and esters, non-ionic surfactants, fungicides, dyes and perfumes may be added to the hair rinse composition of the present invention in the conventional amounts.

In order further to explain the characteristic features of the present invention, illustrative examples of the present invention will now be described.

EXAMPLE 1

Evaluation of Rinsing Effect

A bundle of hairs (human hair) having a length of 15 cm and a diameter of 2 cm was immersed for 5 seconds in 200 ml of a solution containing 2 wt.% of a hair rinse composition maintained at 40° C. Then, the hair bundle was washed for 30 seconds 2 times with 200 ml of warm water maintained at 40° C. and then dried. The touch, suppleness, wetness and smoothness of the hair bundle were evaluated by a panel of 10 women. The results are shown in Table 1.

Conventional hair rinse composition (sample A):

| | |
|---|---|
| Stearylbenzyldimethyl ammonium | 3.0% by weight |

-continued

| | | |
|---|---|---|
| chloride | | |
| Cetyl alcohol | 2.0% | by weight |
| Propylene glycol | 5.0% | by weight |
| Water | 90.0% | by weight |

Hair rinse composition of present invention (sample B):

| | | |
|---|---|---|
| Stearylbenzyldimethyl ammonium chloride | 3.0% | by weight |
| Secondary alcohol ethoxylate (average carbon number = 13.2, average mole number of added ethylene oxide = 3) | 2.0% | by weight |
| Propylene glycol | 5.0% | by weight |
| Water | 90.0% | by weight |

Table 1

| Evaluation of Rinsing Effect | | |
|---|---|---|
| A is better | no difference | B is better |
| zero woman | 3 women | 7 women |

As will be apparent from the results shown in Table 1, the hair rinse composition (sample B) of the present invention is superior to the conventional hair rinse composition (sample A) with respect to the rinsing effect.

EXAMPLE 2

Hair rinse compositions including a secondary alcohol ethoxylate indicated below were evaluated with respect to the rinsing effect according to the method described in Example 1. The results are shown in Table 2.

Basic Recipe:

| | | |
|---|---|---|
| Stearyldimethylbenzyl ammonium chloride | 3.0% | by weight |
| Secondary alcohol ethoxylate | 2.0% | by weight |
| Propylene glycol | 5.0% | by weight |
| Water | 90.0% | by weight |

Secondary Alcohol Ethoxylates Used:

| Average Carbon Number | Average Added EO Mole Number | Sample | |
|---|---|---|---|
| 13.2 | 0 | C | |
| 13.2 | 3 | D | |
| 13.2 | 5 | E | |
| 13.2 | 7 | F | |
| 13.2 | 9 | G | (control) |
| 16.4 | 7 | H | |
| 16.4 | 9 | I | (control) |

Table 2

| samples compared | D is better | no difference | Other sample is better |
|---|---|---|---|
| D-C | 4 | 3 | 3 |
| D-E | 5 | 2 | 3 |
| D-F | 6 | 2 | 2 |
| D-G | 8 | 2 | 0 |
| D-H | 4 | 3 | 3 |
| D-I | 9 | 1 | 0 |

As will be apparent from the results shown in Table 2, the rinsing effect is highest when the average mole number of added ethylene oxide units is zero to 7. When the average mole number of added ethylene oxide units is larger than 7, the rinsing effect is considerably reduced.

In the range wherein the average mole number of added ethylene oxide units is 1 to 7, the rinsing effect is gradually diminished as the mole number of added ethylene oxide units is increased. This tendency can be moderated to some extent by increasing the average carbon number in the alkyl group.

Preferred recipes of hair rinse compositions according to the present invention will now be described.

| Composition Example 1 | |
|---|---|
| Stearyltrimethyl ammonium chloride | 2.0% by weight |
| Secondary alcohol (average carbon number - 13.2, average EO mole number = zero) | 2.0% by weight |
| Propylene glycol | 10.0% by weight |
| Ethanol | 5.0% by weight |
| Perfume and dye | minor amounts |
| Water | 81.0% by weight |

| Composition Example 2 | |
|---|---|
| Stearyltrimethyl ammonium chloride | 2.0% by weight |
| Secondary alcohol ethoxylate (average carbon number - 13.2, average EO mole number - 3) | 2.0% by weight |
| Cetyl alcohol | 2.0% by weight |
| Propylene gycol | 10.0% by weight |
| Perfume and dye | minor amounts |
| Water | 84.0% by weight |

| Composition Example 3 | |
|---|---|
| Distearyldimethyl ammonium chloride | 3.0% by weight |
| Secondary alcohol ethoxylate (average carbon number - 13.2, average EO mole number - 5) | 2.0% by weight |
| Glycerin | 10.0% by weight |
| Perfume and dye | minor amounts |
| Water | 85.0% by weight |

| Composition Example 4 | |
|---|---|
| Di(β-hydroxystearyl)dimethyl ammonium chloride | 3.0% by weight |
| Secondary alcohol ethoxylate (average carbon number - 16.4, average EO mole number - 5) | 4.0% by weight |
| Glycerin | 20.0% by weight |
| Water | 73.0% by weight |

Each of the foregoing compositions has an excellent rinsing effect.

The embodiments of the invention in which an exclusive property or privilege is claimed are defined as follows:

1. A liquid hair rinse composition consisting essentially of
   (a) from 0.1 to 10 percent by weight of one or a mixture of quaternary ammonium salts having the formula

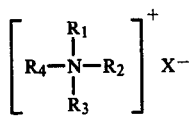

wherein each of $R_1$, $R_2$, $R_3$ and $R_4$ is alkyl, hydroxyalkyl or benzyl, with the proviso that one or two of $R_1$, $R_2$, $R_3$ and $R_4$ is alkyl having 8 to 20 carbon atoms or hydroxyalkyl having 8 to 20 carbon atoms and the remainder of $R_1$, $R_2$, $R_3$ and $R_4$ are alkyl having one to 3 carbon atoms, hydroxyalkyl having one to 3 carbon atoms or benzyl, and X is halide, methylsulfate or ethyl sulfate, (b) from 0.1 to 10 percent by weight of a synthetic secondary alcohol prepared by oxidizing normal paraffin or an ethoxylate thereof, said alcohol having the formula

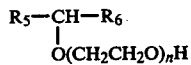

wherein n is a number from zero to 7 and

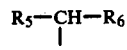

is alkyl having 12 to 18 carbon atoms, and (c) an amount of a water-miscible organic solvent effective to dissolve components (a) and (b), and (d) the balance consists essentially of water.

2. A hair rinse composition as claimed in claim 1, containing from 0.5 to 7 percent by weight of (a), and from 0.5 to 5 percent by weight of (b).

3. A hair rinse composition as claimed in claim 1, containing from one to 4 percent by weight of (a), and from one to 4 percent by weight of (b).

4. A hair rinse composition as claimed in claim 3, in which n is a number from zero to 3.

5. A hair rinse composition as claimed in claim 1 in which X is chloro, bromo or iodo.

6. A hair rinse composition as claimed in claim 1 in which X is methyl sulfate or ethyl sulfate.

7. A hair rinse composition as claimed in claim 1 in which (a) is stearylbenzyldimethyl ammonium chloride.

8. A hair rinse composition as claimed in claim 1 in which (a) is stearyltrimethyl ammonium chloride.

9. A hair rinse composition as claimed in claim 1 in which (a) is distearyldimethyl ammonium chloride.

10. A hair rinse composition as claimed in claim 1 in which (a) is di-($\beta$-hydroxystearyl)dimethyl ammonium chloride.

* * * * *